US010963601B2

United States Patent
McCloskey et al.

(10) Patent No.: US 10,963,601 B2
(45) Date of Patent: Mar. 30, 2021

(54) HEAD-MOUNTED DISPLAY AND/OR VIRTUAL REALITY VIDEO OUTPUT AND MAPPING HANDHELD INPUT DEGREES-OF-FREEDOM TO PROPERTIES OF MOLECULAR STRUCTURE

(71) Applicants: Nanome, Inc., San Diego, CA (US); The Regents of the University of California, Oakland, CA (US)

(72) Inventors: Steven Robert McCloskey, San Diego, CA (US); Taylor Philip Horwood, Auckland (NZ); Keita William Funakawa, San Diego, CA (US); Benjamin Hugh Bratton, San Diego, CA (US)

(73) Assignees: Nanome, Inc., San Diego, CA (US); The Regents of the University of California, Oakland, CA (US)

( * ) Notice: Subject to any disclaimer, the term of this patent is extended or adjusted under 35 U.S.C. 154(b) by 891 days.

(21) Appl. No.: 15/604,305

(22) Filed: May 24, 2017

(65) Prior Publication Data
US 2017/0344674 A1    Nov. 30, 2017

Related U.S. Application Data

(60) Provisional application No. 62/341,869, filed on May 26, 2016.

(51) Int. Cl.
| | |
|---|---|
| G06F 30/20 | (2020.01) |
| G16C 10/00 | (2019.01) |
| G06F 3/0354 | (2013.01) |
| G06F 3/0484 | (2013.01) |
| G06F 3/01 | (2006.01) |
| G06F 3/0346 | (2013.01) |
| G06F 3/0481 | (2013.01) |
| G06F 1/16 | (2006.01) |
| G16C 20/30 | (2019.01) |
| G16B 15/00 | (2019.01) |
| G16C 20/00 | (2019.01) |
| G16C 60/00 | (2019.01) |
| G06T 19/00 | (2011.01) |
| G16C 20/80 | (2019.01) |

(52) U.S. Cl.
CPC ............. *G06F 30/20* (2020.01); *G06F 1/163* (2013.01); *G06F 3/011* (2013.01); *G06F 3/0346* (2013.01); *G06F 3/03547* (2013.01); *G06F 3/04815* (2013.01); *G06F 3/04845* (2013.01); *G06T 19/006* (2013.01); *G16B 15/00* (2019.02); *G16C 10/00* (2019.02); *G16C 20/00* (2019.02); *G16C 20/30* (2019.02); *G16C 60/00* (2019.02); *G16C 20/80* (2019.02)

(58) Field of Classification Search
None
See application file for complete search history.

(56) References Cited

U.S. PATENT DOCUMENTS

2015/0199034 A1    7/2015    Armstrong

FOREIGN PATENT DOCUMENTS

WO    WO 2016054613 A1    4/2016

OTHER PUBLICATIONS

Ai, Zhuming, and Torsten Fröhlich. "Molecular dynamics simulation in virtual environments." Computer Graphics Forum. vol. 17. No. 3. Oxford, UK and Boston, USA: Blackwell Publishers Ltd, 1998.*
Barlian, A. Alvin, et al. "Semiconductor piezoresistance for microsystems." Proceedings of the IEEE 97.3 (2009): 513-552.*
Gillet et al., Tangible Interfaces for Structural Molecular Biology, Structure, Mar. 2005, vol. 13:3, pp. 483-491.
Stone et al. Immersive Molecular Visualization and Interactive Modeling with Commodity Hardware, In: Advances in Visual Computing, 6th International Symposium, ISVC 2010, edited by Bebis et al., Sprigner-Verlag Berlin Heidelberg, 2010, vol. LNCS 6454, pp. 382-393.
Waldon et al., SketchBio: a scientist's 3D interface for molecular modeling and animation, BMC Bioinformatics, Oct. 30, 2014, vol. 15, Article No. 334, pp. 1-17.
International Search Report for PCT/US2017/034472 dated Aug. 29, 2017.
Cserti, József, et al., "Uniform tiling with electrical resistors" *J. Phys. A: Math. Theor.* 44 (2011) 215201 (20pp).

* cited by examiner

*Primary Examiner* — G Steven Vanni
(74) *Attorney, Agent, or Firm* — Knobbe, Martens, Olson & Bear, LLP

(57) ABSTRACT

A system and method for molecular design and simulation is disclosed. In one aspect, a system for simulating a molecular structure includes a processor configured to simulate the molecular structure, a head-mounted display (HMD) configured to display the molecular structure, and at least one handheld input device. The input device may be configured to: receive input from a user, the input being indicative of movement of the handheld input device in 6 degrees-of-freedom (DoF), and selectively map, based on additional user input and at least one property of the molecular structure, one of the DoF to one of a plurality of defined techniques for altering the molecular structure. The processor may be configured to modify the molecular structure based on the received input as mapped to the selected defined technique.

17 Claims, 7 Drawing Sheets

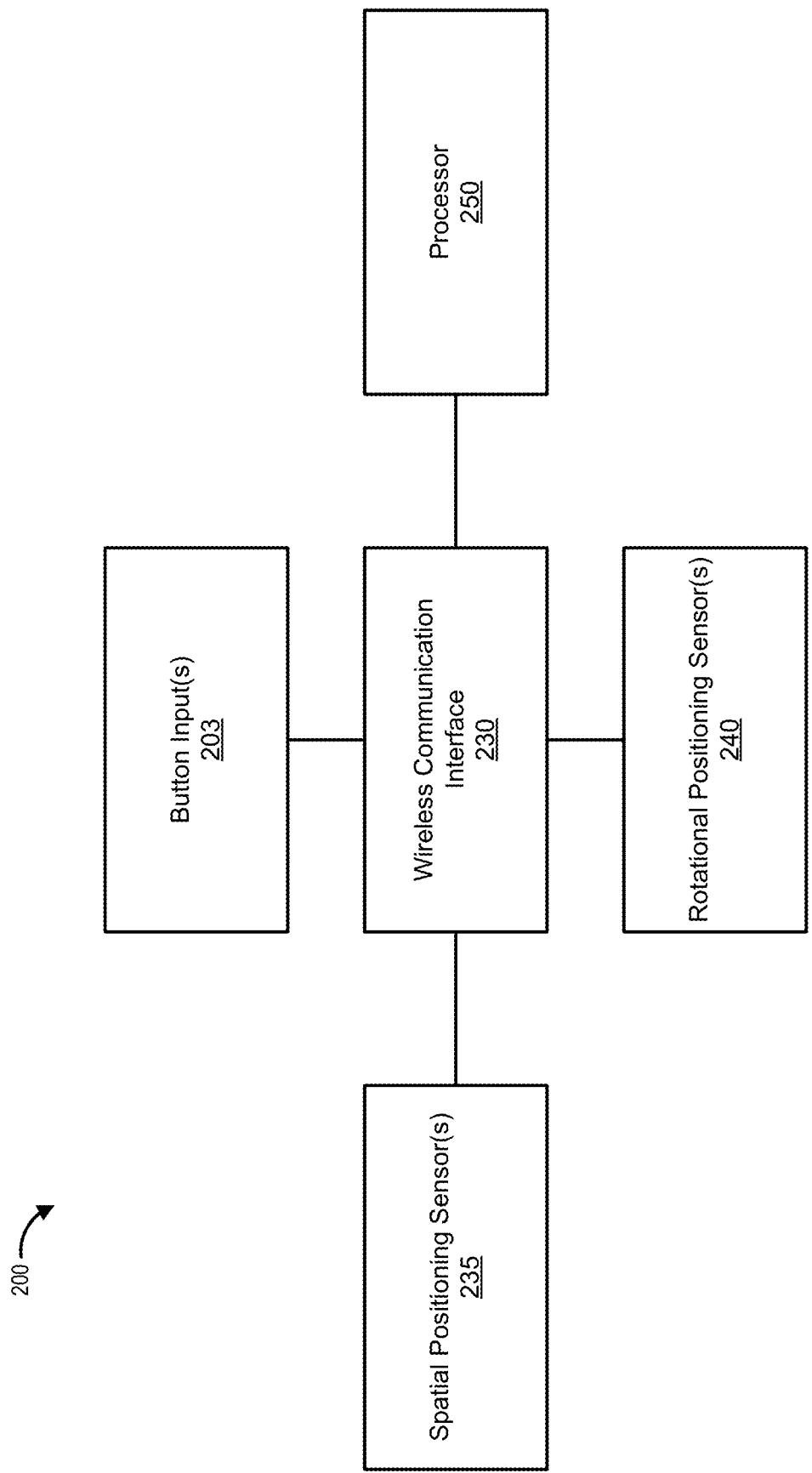

HEAD-MOUNTED DISPLAY AND/OR VIRTUAL REALITY VIDEO OUTPUT AND MAPPING HANDHELD INPUT DEGREES-OF-FREEDOM TO PROPERTIES OF MOLECULAR STRUCTURE

CROSS-REFERENCE TO RELATED APPLICATIONS

This application claims the benefit of U.S. Provisional Application No. 62/341,869, filed May 26, 2016, which is herein incorporated by reference in its entirety.

BACKGROUND

Technological Field

The disclosed technology relates generally to molecular design and simulation, and more particularly, to user interactions with a molecular design and simulation system.

Description of the Related Technology

Research and design of molecular, atomic and/or sub-atomic structures can be performed via the use of simulation software running on a computer. These systems can store information related to the particular structure(s) being simulated and the simulation of the structures can be based on a mathematic approximation of the physical and/or chemical interactions between the atomic and/or sub-atomic particles that make up the simulated structure(s).

SUMMARY OF CERTAIN INVENTIVE ASPECTS

The systems, methods and devices of this disclosure each have several innovative aspects, no single one of which is solely responsible for the desirable attributes disclosed herein.

In one aspect, there is provided a system for simulating a molecular structure. The system may include a processor configured to simulate the molecular structure; a head-mounted display (HMD) configured to display the molecular structure; and at least one handheld input device configured to: receive input from a user, the input being indicative of movement of the handheld input device in 6 degrees-of-freedom (DoF), and selectively map, based on additional user input and at least one property of the molecular structure, one of the DoF to one of a plurality of defined techniques for altering the molecular structure, wherein the processor is configured to modify the molecular structure based on the received input as mapped to the selected defined technique.

In another aspect, there is provided a system, including a processor configured to simulate a molecular structure; and at least one input device configured to: receive input from a user, the input being indicative of movement of the input device in 6 degrees-of-freedom (DoF), and selectively map, based on additional user input and at least one property of the molecular structure, one of the DoF to one of a plurality of defined techniques for altering the molecular structure.

In yet another aspect, there is provided method for simulating a molecular structure. The method may involve generating a virtual-reality (VR) video stream including the molecular structure; receiving input from at least one handheld device, the received input being indicative of movement of the handheld input device in 6 degrees-of-freedom (DoF); selectively mapping, based on additional user input and at least one property of the molecular structure, one of the DoF to one of a plurality of defined techniques for altering the molecular structure; and modifying the molecular structure based on the received input as mapped to the selected defined technique.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIGS. 2A and 2B illustrate an embodiment of an input device in accordance with aspects of this disclosure.

DETAILED DESCRIPTION OF CERTAIN ILLUSTRATIVE EMBODIMENTS

Embodiments of this disclosure relate to systems and techniques for the simulation and design of molecular structures based on the atomic and/or sub-atomic information of the structure being simulated. Aspects of this disclosure relate to the simulation of such structures over a vast range of scales, which may on the low end include structures comprised of known and/or theoretical sub-atomic particles. Larger scale structures can be built from these sub-atomic particles or atomic particles and, via the combination of these particles, form increasingly large and complex structures by adding additional particles to the structure. The size of a simulated structure is only limited on the upper end by the memory and processing capabilities of the systems (e.g., computer(s) and/or server(s)) performing the simulation. For convenience of description, as used herein, a "molecular structure" can refer to any of the above-described structures which can be simulated by a computer system, including sub-atomic, atomic, biological, pharmaceutical, and semiconductor materials, along with any other structures which can be built via a combination of such structures. Thus, the term "molecular structure" is not limited to the molecular scale unless the context of the corresponding description so requires.

Figure 1:
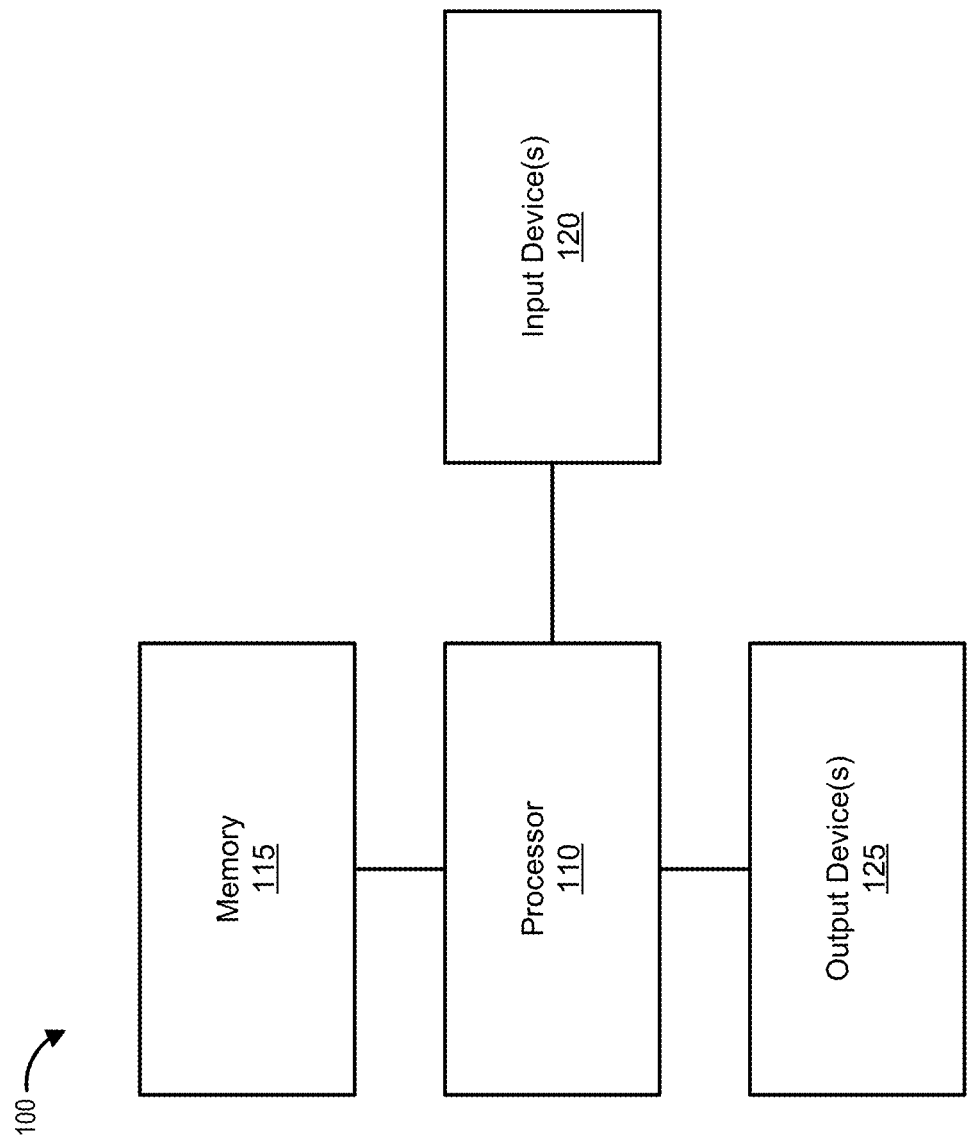
FIG. 1 is an exemplary computer system which can simulate molecular structures in accordance with aspects of this disclosure.

FIG. 1 is an exemplary computer system which can simulate molecular structures in accordance with aspects of this disclosure. The system 100 illustrated in FIG. 1 includes a processor 110, a memory 115, one or more input device(s) 120, and one or more output device(s) 125. Additional processors 110 and/or memories 115 may also be included without departing from this disclosure.

The processor 110 can perform mathematical calculations associated with the simulation and/or design of molecular structures. The processor 110 can also be configured to perform various tasks associated with receiving information and/or instructions from the input device(s) 120 and providing information to be displayed via the output device(s) 125. The output device(s) 125 can be configured to provide feedback to the user via techniques other than the traditional display of images, including via haptic feedback and other feedback techniques as will be described in greater detail below. The memory 115 can store information relating to the simulation of the molecular structures, along with any other required instructions for execution by the processor 110 in the performance of tasks associated with the simulation of the molecular structure and/or communication with the input device(s) 120 and output devices (125). In certain embodiments, the memory 115 is a non-transitory computer readable storage medium which stores instructions for execution by the processor 110.

Figure 2A:
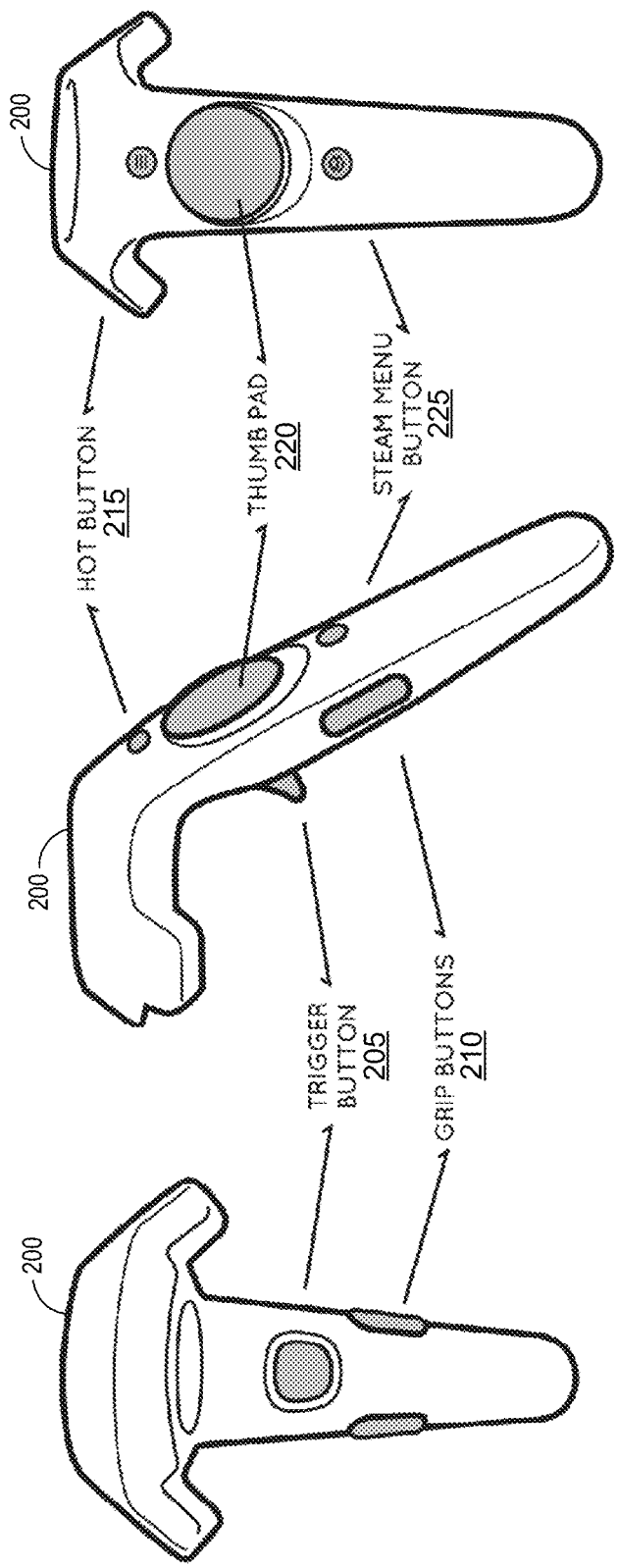

FIGS. 2A and 2B illustrate an embodiment of an input device in accordance with aspects of this disclosure. Specifically, FIG. 2A illustrates a physical controller 200 (also referred to as a handheld input device or simply as a controller) which can be held by a user of the system 100. One example of a controller 200 is the HTC Vive™ controller. However, this disclosure is not limited to this example and other input device(s) can be used as the input device(s) 120 without departing from this disclosure, examples of which are provided below.

In the FIG. 2A embodiment, the controller 200 is designed to be held by a user of the system 100 via one of the user's hand and includes a number of buttons 205, 210, 215, 220, and 225, which may be located to be actuated (e.g., pressed) by one of the user's fingers in use. When embodied as an HTC Vive™ controller, these buttons may include a trigger button 205, one or more grip button(s) 210, a hot button 215, a thumb pad 220, and/or a steam menu button 225. These buttons may be digital buttons, having on/off states or may be analog buttons, including a plurality of states between fully open and fully pressed. One or more of the buttons 205-225 can also be embodied as a trackpad, enabling the user to move one or more fingers along the trackpad indicating a 2D position of the user's finger. The user can interact with the system via one or more controllers 200 (typically one or two controllers 200) via the actuation of the various buttons 205-225 as well as by moving the controllers through space.

FIG. 2B illustrates a number of components which may be included in one of the input device(s) 120 and/or in the controller 200 illustrated in FIG. 2A in accordance with aspects of this disclosure. For example, the controller 200 may include button inputs 203 (such as buttons 205 to 225), a wireless communication interface 230, spatial positioning sensor(s) 235, rotational sensor(s) 240, and a processor 250. The wireless interface 230 may be configured to communicate with a corresponding wireless interface (not illustrated) of the system 100 in communication with the processor 110 in order to communicate therewith. However, the controller 200 is not limited to a wireless interface 230 and in other embodiments, can include a wired interface (not illustrated) connected to a corresponding wired interface (not illustrated) of the processor 110.

The spatial sensor(s) 235 can determine the spatial positioning (also referred to as translational positioning) of the controller 200 while the rotational sensor(s) 240 can determine the rotational positioning of the controller 200. The spatial sensor(s) 234 and rotational sensor(s) 240 may be entirely self-sufficient or may function with the aid or one or more base stations (not illustrated). In some embodiments, the spatial and rotational sensor(s) 235 and 240 (which may be referred to together as positioning sensor(s) 235 and 240) may also be combined into a single sensor which can produce information from which the spatial and rotational positioning of the controller 200 can be determined by the processor 250 and/or the processor 110. In one embodiment, the positioning sensor(s) 235 and 240 can include a gyroscope. In another embodiment, the positioning sensor(s) 235 and 240 can include one or more light-emitting diodes (LEDs) (not illustrated). The base station(s) can detect light emitted from the LEDs and the processor 110 can calculate the position of the LEDs (and thus the controller 200) based on the location of the light within the field of view of the images obtained by the base stations. In another embodiment, the base station(s) may emit light which photodetectors (not illustrated) positioned on the controller 200 may detect, from which the processor(s) 250 and/or 110 may determine the positioning of the controllers. In yet another embodiment, other signals may be detected by one or more of the base station(s) and the controller 200, such as acoustic signals, magnetic signals, etc. In still other embodiments, the controller 200 may be able to map the environment without the need of base stations, for example, by building a model of the environment from images obtained by image sensor(s) located on the controller 200.

The spatial sensor(s) 235 and the rotational sensor(s) 240, together with the processor 250 enable the controller 200 to measure the spatial and angular positions of the controller 200, along with changes thereto, thereby enabling the user to move and/or rotate the controller 200 as input to the system 100. These types of movement and rotation of the controller 200 by the user may be referred to generally as "gestures". The controller 200 is configured to interpret the 6DoF movement of the controller as input received from a user. As discussed in greater detail below, the controller 200 can be configured to map at least one of the DoF of the controller 200 to one of a plurality of defined techniques for altering the molecular structure. This mapping can be performed in response to user input (e.g., the actuation of one of the buttons 205-225) and based on at least one of the properties of the molecular structure.

Since the main body of the controller is rigid, the movement and rotation of the controller may be defined by six degrees-of-freedom (6Dof) of movement of a rigid body in free space. These include the spatial position of the rigid body, which may be measured with respect to a defined coordinate system along three axes (e.g., the X-axis, Y-axis, and Z-axis). The rotational degrees of freedom may be defined as rotational movement along three rotational axes (e.g., roll, pitch, and yaw). Thus, the spatial positioning of the controller 200 may be defined at any given point in time by six values representative of the controller's 200 6DoF. The above-describes coordinate systems are merely exemplary and any other method of defining the 6DoF of the controller 200 may be used without departing from the disclosure. For example, polar coordinate and spherical coordinate systems can also be used.

Although a hand-held controller 200 is described above, the described technology can be applied to other types of input device(s) 120. For example, the communication between the controller 200 and one or more base stations can be based on an electromagnetic (EM) signal passed therebetween. In one implementation, the base station(s) may generate an EM signal which the controller can detect using the positioning sensor(s) 235 and 240 to determine the 6DoF positioning of the controller 200. In another embodiment, communication between the controller 200 and the base stations is based on light emitted from either the controller 200 or the base station(s). As described above, the controller 200 can include LEDs which emit light detected by the base station(s), from which the 6DoF of the controller 200 can be determined. Alternatively, the positioning sensor(s) 235 and 240 of the controller 200 can detect light emitted from LEDs on the base station(s).

In another embodiment, the controller 200 can calculate the 6DoF positioning of the controller without a base station using an ultrasonic transmitter and detector. For example, the controller 200 can emit an ultrasonic signal and based on the reflected signals received at the ultrasonic detector, generate a map of the environment. Changes to the map generated based on the signal received by the ultrasonic detector can be used by one or more of the processors 110 and 250 to determine the position of the controller 200. In another embodiment, the controller 200 can generate a map of the environment using a camera provided on the controller 200 rather than an ultrasonic system. Thus, the environment can be mapped visually by extracting features from the images obtained using the camera to derive the position of the controller 200.

In yet another embodiment, stereo cameras, provided on base station(s) can be used to map the positioning of the user's hands. In this embodiment, the user does not require a physical controller 200, but rather, can use his/her hands as input device(s) directly. Thus, the user can position his/her hands and form various shapes with his/her hands which can be detected by the stereo cameras in the base station(s). Similar to the use of a controller 200, the 6DoF of the user's hands can be determined and mapped to various techniques for interacting with a molecular structure.

Figure 3:
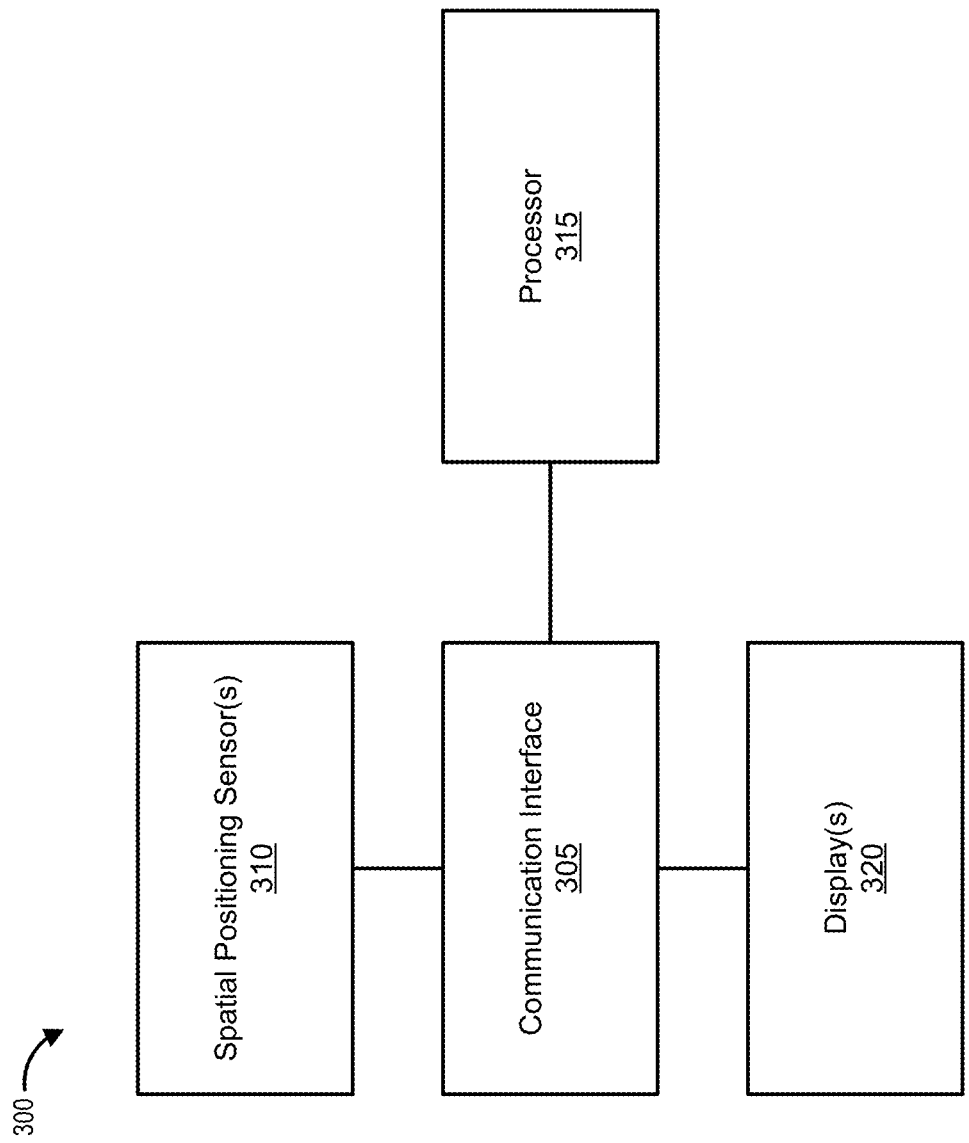
FIG. 3 is an illustration of an exemplary output device in accordance with aspects of this disclosure.

FIG. 3 is an illustration of an exemplary output device in accordance with aspects of this disclosure. The output device 300 is configured to display images received from the processor 110. For example, the output device 300 can display the simulated molecular structure. In certain embodiments, the output device 300 of FIG. 3 may be a head-mounted display (HMD) and can include a communication interface 305, spatial positioning sensor(s) 310, a processor 315, and display(s) 320. The communication interface 305 may be a wired or wireless interface configured to communicate with the processor 110 of the system 100. The processor 315 can be configured to receive information from the processor 110 of the system 100 and format the received information for display via the display(s) 320. When embodied as an HMD 300, the display(s) 320 can include one display, split using a system of optical elements (not illustrated) to provide separate images to the user's left and right eyes. Alternatively, the display(s) 320 can include two displays which are configured to generate images dedicated to a corresponding one of the user's eyes. The two images provided to the user can simulate depth such that the user perceives a three-dimensional representation of the displayed images, such as the simulated molecular structure.

The spatial positioning sensor(s) 310 can be implemented as any one of the sensor(s) described above in connection with the spatial sensor(s) 235 and the rotational sensor(s) 240 of the controller 200. In an exemplary implementation, the spatial positioning sensor(s) 310 are embodied as LEDs which emit light that can be detected by base stations (not illustrated). The positioning of the HMD 300 can be calculated by the processor 110 based on signal(s) received from the base station(s). Using the known position of the HMD 300, the processor 110 can generate images that correspond to the position of the user's eyes within the environment generated by the displayed images. For example, as the user moves his/her head within the simulated environment, the images sent to the display(s) 320 are updated correspondingly allowing the user to experience the simulated environment as though he/she was present in the environment. Such systems can be generally referred to as virtual reality (VR) systems.

The output device 300 can also be embodied as an augmented reality (AR) display. An AR display can display an image overlaid on the real environment by either allowing light to pass through the display(s) 320, or by capturing an image from a camera (not illustrated) mounted on the output device 300 and displaying the image, augmented by images provided from the system 100, to the user via the display(s) 320.

However, the described technology is not limited to output devices which may be head-mounted, and may also display the simulated molecular structure using a traditional 2D display and/or any other type of visual display device. Additionally, output device(s) 125 may include feedback mechanisms using techniques other than visual feedback, such as haptic feedback. Examples of haptic feedback which can be employed by the output device(s) 125 include: color feedback, acoustic feedback, tactile feedback, etc.

Modification of a Molecular Structure

Embodiments of the above-described system 100 can simulate molecular structures and enable a user to interact with the simulated structures as well as modify the structures. In order to simulate a molecular structure, the memory 115 can store the atomic properties and spatial position for each atom and/or sub-atomic particle in the structure. The memory 115 may also store bond information between the atoms of the molecular structure. As previously discussed, larger simulated molecular structures, such as a pharmaceutical structure, may require the storage of a larger amount of positioning and atomic information than a simpler molecular structure. Examples of data storage formats for such molecular structures include crystallographic information file (CIF), macromolecular CIF (MMCIF), structure-data file (SDF), molfile, and protein data bank (PDB) files. However, this disclosure is not limited thereto and aspects of this disclosure can use any storage format which can encode information that can be used to reconstruct a molecular structure.

The simulation of a given molecular structure can also depend on the type of molecular structure being simulated. For example, in a quantum scale simulation, the processor 110 can simulate the interactions between the atomic and/or sub-atomic particles using the Schrödinger equation for energy. Larger molecules can be simulated using classical molecular dynamics. The specific techniques used to simulate a given molecular structure may be selected by the user or may be automatically determined by the processor 110 based on the size of the molecular structure being simulated.

In a traditional molecular structure simulation system, the user can interact with and/or design the molecular structure using traditional input/output devices, such as a keyboard, mouse and monitor. However, these input/output devices may be limited in the way the molecular structure is displayed to the user as well as in the way the user is able to interact with the molecular structure. For example, molecular structures are commonly complex three-dimensional (3D) structures. Accordingly, displaying such a structure on a traditional two-dimensional (2D) monitor may block certain portions from view since these portions may be obstructed by another portion of the molecular structure closer to the point of view of the user. Similarly, a keyboard and/or mouse may present difficulties in precisely positioning and/or interacting with a molecular structure. For example, the user can move a mouse in 2D, but moving a specified atom around in 3D space using the 2D input of a mouse can be limiting and/or difficult.

Aspects of this disclosure therefore relate to input and output devices and techniques which provide a user with a more intuitive and/or efficient interface for interacting with a molecular structure. In particular, certain aspects of this disclosure relate to the mapping of one or more of the 6DoF of an input device 120 to one of a plurality of defined techniques for modifying the structure of a plurality of the particles in the molecular structure. In certain embodiments, the specific technique for manipulating the molecular structure may be based on the type and/or scale of the molecular structure.

Although aspects of this disclosure are described herein in connection with a single user modifying a molecular structure, this disclosure is not limited to a single user. For example, a plurality of users may each be connected to the system 100 via their own input device(s) 120 and output device(s) 125. When multiple users connect to the system 100, the users may connect via a personal computer (PC) connected to a server (not illustrated). The server may store data related to the simulated molecular structure such that each user can view and manipulate the same copy of the molecular structure. As such, modifications made to the molecular structure by one user can also be viewed by another user. The plurality of users can view and/or modify the molecular structure simultaneously or asynchronously.

In one embodiment, the molecular structure can be modified using a transformation matrix S which defines the method(s) for altering the molecular structure. An example of one such transformation matrix S is shown below.

$$\begin{bmatrix} S_X & 0 & 0 \\ 0 & S_Y & 0 \\ 0 & 0 & S_z \end{bmatrix}$$

The above-illustrated transformation matrix S may be used to define the size of the molecular structure in 3D. For example, the values $S_X$, $S_Y$, and $S_Z$ (which are also referred to as "scaling values" herein) in the transformation matrix S can be used to define the scaling of the size of the molecular structure along the corresponding X, Y, and Z-axes. As used herein, the scaling of the molecular structure generally refers to increasing or decreasing the number of particles comprising the molecular structure in the corresponding X, Y, and Z-axes based on the values $S_X$, $S_Y$, and $S_Z$ in the transformation matrix S, rather than simply altering the apparent size of the molecular structure as displayed by the output device(s) 125 or 300. That is, changes in the values $S_X$, $S_Y$, and $S_Z$ in the transformation matrix S define changes to the structure of the molecular structure.

In one embodiment, doubling the value of $S_X$ will result in a doubling of the size of the molecular structure in the X-axis. The values of $S_X$, $S_Y$, and $S_Z$ can each be altered to proportionally modify the scale of the molecular structure in the corresponding axes. However, in other embodiments, the modification of the scale of the molecular structure along each of the axes can be related to the values $S_X$, $S_Y$, and $S_Z$ by other functions, such as via exponential, linear, logarithmic, etc. functions.

In an exemplary embodiment, each of the values $S_X$, $S_Y$, and $S_Z$ of the transformation matrix S can be mapped to the corresponding spatial position DoF of the controller 200. The mapping of the values $S_X$, $S_Y$, and $S_Z$ of the transformation matrix S to the spatial DoF of the controller 200 can be performed based on user input and based on at least one property of the molecular structure. Thus, in one embodiment, the scale of the molecular structure along the X-axis can be altered by the user moving the controller 200 in space along the X-axis. The user can also modify the scale of the molecular structure along more than one axis simultaneously. For example, the user can move the controller along the X-Y plane to alter the scale of the molecular structure in each of the X and Y-axes, and similarly, the user can modify the scale of the molecular structure in all three dimensions (e.g., along each of the X, Y, and Z-axes) by moving the controller 200 in all three dimensions simultaneously.

The user can input a command to the system 100 in order to modify the scale of the molecular structure via actuation of one or more of the buttons 205-225. In one implementation, the user can "grab" the molecular structure by placing a first controller within a threshold distance of a portion of the molecular structure and pressing one of the buttons 205-225 on the first controller 200. Thereafter, the user may press another button 205-225 on a second controller 200 and alter the distance between the two controllers 200. The change in the distance between the two controllers 200 can be used as input received by the processor 110 of the system 100 to alter the values $S_X$, $S_Y$, and $S_Z$ of the transformation matrix S based on the relative movement of the two controllers 200 with respect to the X, Y, and Z-axes.

In addition to mapping the spatial DoF to the values $S_X$, $S_Y$, and $S_Z$ of the transformation matrix S, the rotational DoF of the controller 200 (e.g., roll, pitch, and yaw) can be mapped to modify certain properties of the molecular structure. In certain implementations, the mapping of the 6DoF of the controller 200 to one or more techniques for modifying the molecular structure can be selectively controlled by the user by actuating one of the buttons on the controller 200.

Furthermore, the mapping of each of the 6DoF of the controller 200 to technique(s) for modifying the molecular structure can be based on the properties of the molecular structure being simulated. Examples of the properties of the molecular structure which can be used to determine the specific mapping between the 6DoF and the techniques for modifying the molecular structure include: the type of the molecular structure, the scale of the molecular structure, the base building blocks (e.g., atoms, sub-atomic particles, proteins, crystal, deoxyribonucleic acid (DNA), carbon nanotubes, etc.) used to construct the molecular structure, etc.

In an exemplary embodiment, the molecular structure can be a crystal lattice. In this embodiment, the mapping of the 6DoF of the controller 200 to techniques for modifying the crystal lattice can be based on the molecular structure being a crystal lattice (e.g., the processor 110 can automatically perform this mapping in response to determining that the molecular structure is crystalline). Since a crystal lattice can be extended in each of the spatial directions (e.g., along each of the X, Y, and Z-axes), the spatial positioning DoF of the controller 200 can be mapped to corresponding changes in the scale of the molecular structure along these axes (e.g., via altering the values $S_X$, $S_Y$, and $S_Z$ in the transformation matrix S as discussed above).

In one embodiment, the rotational DoF of the controller 200 for a crystalline molecular structure can be mapped to values representative of the Miller plane of the crystal lattice. In another embodiment, the rotational DoF of the controller 200 can be encoded as values in the transformation matrix S, e.g., in place of at least some of the values of the transformation matrix S having the value 0 as shown above. For example, the roll of the controller 200 can be mapped to the (2,3) and (3,2) locations, the pitch of the controller 200 can be mapped to the (1,3) and (3,1) locations, and the yaw of the controller 200 can be mapped to the (1,2) and (2,1) locations of the transformation matrix S. Since each rotational DoF can be mapped to two locations within the transformation matrix S, the user may be able to modify one of the values by rotating the controller 200 in the corresponding positive direction (e.g., in the positive yaw direction) and the other of the values by rotating the controller 200 in the corresponding negative direction (e.g., in the negative yaw direction). Changes to these values of the transformation matrix S can modify the structure of the crystal lattice, providing the user with additional techniques for modifying the molecular structure. The processor 110 can be configured to perform the mapping of at least one of the rotational DoF of the controller to a defined technique for modifying the Miller plane in response to determining that the molecular structure is a crystalline molecular structure.

Changes to the Miller plane of a given crystalline molecular structure may be useful in molecular design since these changes can have an effect on certain properties of the structure. For example, changes to the Miller plane of the crystalline molecular structure can affect the resistance of the structure. Accordingly, a feedback mechanism can be provided to the user via output device 300, allowing the user to view in real time the changes to the resistance of the crystalline molecular structure as the user rotates the controller 200, modifying the Miller plane of the crystal lattice.

In the crystalline molecular structure embodiment, the user may also specify symmetry conditions. For example, the user can select 3D symmetry conditions which can affect how the molecular structure is produced. The user may, for example, select the 3D symmetry conditions via a menu using the controller 200. In another example, the user can place a plane used to define symmetry (e.g., a mirror plane for mirror symmetry) using the 6DoF of the controller 200. Accordingly, the user can place planes of symmetry via the intuitive positioning of the controller 200 by manipulating the 6DoF of the controller 200.

In another exemplary embodiment, the molecular structure can be a carbon nanotube. Since carbon nanotubes may have a defined structure that can only be scaled in one DoF (e.g., along the length of the carbon nanotube), the system 100 can be configured to map only one of the spatial DoF of the controller 200 to modify the scale of the carbon nanotube. The DoF of the controller 200 mapped to the modification of the scale of the carbon nanotube can be based on the orientation of the carbon nanotube as viewed by the user via the output device 300 and may be continually updated as the user moves within the simulated environment and/or the user repositions the carbon nanotube.

When simulating a carbon nanotube, at least one of the rotational DoF of the controller 200 can be mapped to the chirality of the carbon nanotube. Thus, the user may be able to modify the chirality of the carbon nanotube by rotating the controller 200 in the corresponding rotational DoF. In certain implementations, the chirality of the carbon nanotube may be represented by an angle having a value between 0° and 30°. Thus, in at least one implementation, a rotation of the controller 200 past the maximum or minimum value of the chirality can result in the value being reset. For example, a rotation past a value of 30° can result in the chirality being reset to 0° and increasing with further rotation of the controller 200. Alternatively, the chirality of the carbon nanotube may be altered within a set 30° range of rotation of the controller 200 such that rotation of the controller outside of this range does not alter the chirality of the carbon nanotube.

The chirality value can be displayed to the user via the output device 300 in real time as the user modifies the chirality value. The chirality of the carbon nanotube can also be related to the resistance of the carbon nanotube. As such, the resistance of the carbon nanotube can also be displayed in real time as the user modifies the chirality value to aid in the design of the carbon nanotube by the user.

Rather than a carbon nanotube, the user can also design and/or simulate a carbon ribbon (e.g., a plane of bonded carbon atoms also referred to as a sheet of graphene). In this implementation, two of the spatial DoF of the controller 200 can be mapped to scale the size of the carbon ribbon since the carbon ribbon can be modified along its plane. Thus, the number of DoF of the controller 200 mapped to techniques for modifying the molecular structure can be based on the properties of the molecular structure being modified.

Similar to the mapping of the DoF of the controller 200 to modify the size and properties of a carbon nanotube or carbon ribbon, the 6DoF of the controller 200 can also be generally applied to modify an arbitrary molecular structure having the shape of a manifold or an n-brane membrane. The specific techniques for modifying the scale of the manifold (e.g., via the use of the transformation matrix S) can be based on the chemical interactions between the atoms forming the manifold. Additionally, properties of the manifold can be identified and mapped to the rotational DoF of the controller 200 and the values of these properties can be displayed to the user as the controllers 200 are rotated.

Figure 4:
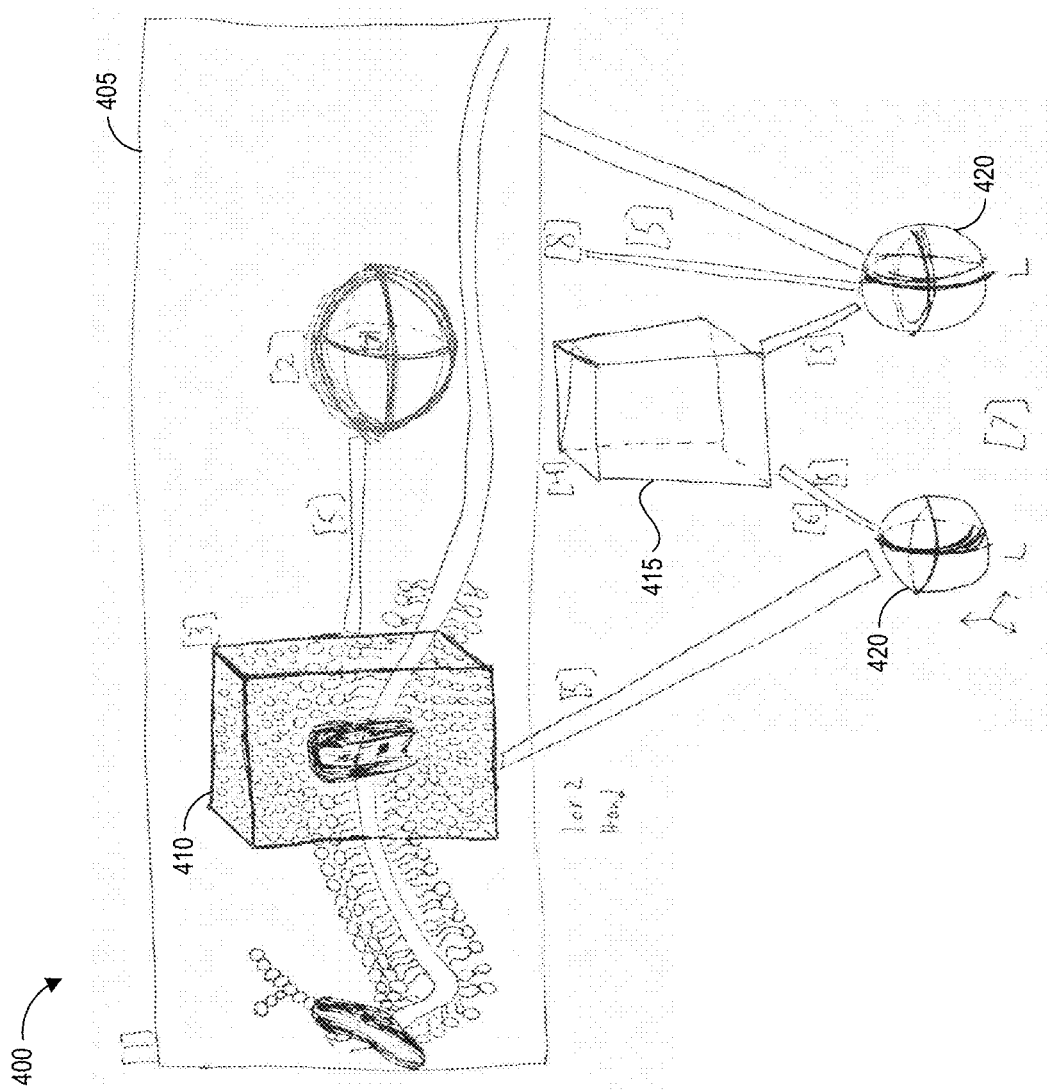
FIG. 4 is an illustration of an exemplary interaction between a user and a simulated molecular structure in accordance with aspects of this disclosure.

FIG. 4 is an illustration of an exemplary interaction between a user and a simulated molecular structure in accordance with aspects of this disclosure. Specifically, FIG. 4 illustrates a virtual environment 400 in which the simulated molecular structure is a large biological structure 405. Although this embodiment is described in connection with a large biological structure 405, the control scheme and techniques described in connection with FIG. 4 can also be applied to other molecular structures in which the user desires to modify only a portion of the molecular structure.

In the FIG. 4 embodiment, the user may desire to modify only a portion of the biological structure 405. Accordingly, the user may select a region 410 of the biological structure 405 on which further modifications are to be performed. In one implementation, the user may select this region 410 by drawing a box around the region 410. However, the user may select the region 410 via any other method, such as by dragging the edges of a box surrounding the region 410 to the desired size.

Once the region 410 has been selected, a copy of the region 415 is generated. The user may modify the properties of the region 410 by interacting with the copy of the region 415. Modifications to the copy of the region 415 may be input to the system 100 by the user via 6DoF movement 420 of one or more controllers 200. Any one of the above-described mappings between the DoF of the controllers 200 as described above can be used to modify the copy of the region 415. Changes to the copy of the region 415 by the user can be reflected automatically to the region 410 of the biological structure 405.

In addition to making changes to the copy of the region 415, the user can also run a simulation of the copy of the region 415 outside of the overall biological structure 405 without making changes to the original region 410. Thus, the user can view the simulation of the selected region 410 and make temporary changes to the copy of the region 415 without affecting the biological structure 415.

In another embodiment, the user may design a molecular structure by placing individual particles and/or molecular structures together. The placement of the particles and/or molecular structures can be performed by a one-to-one movement of the particles/structures with the movement of the controller 200. In one example, the user may pack the particles and/or structures in a volume defined by a mathematical equation. For example, the user may define a sphere having a certain volume and place lipids along the surface of the sphere to create a lipid layer. Thereafter, the user can create a pharmaceutical structure by packing pharmaceutical drugs into the lipid layer sphere, thereby creating a nano-transportation device. However, the packing of particles within a geometric shape is not limited to a sphere and molecular structures can be packing into any geometric shape without departing from aspects of this disclosure.

Plotting of Material Properties

Figure 5:
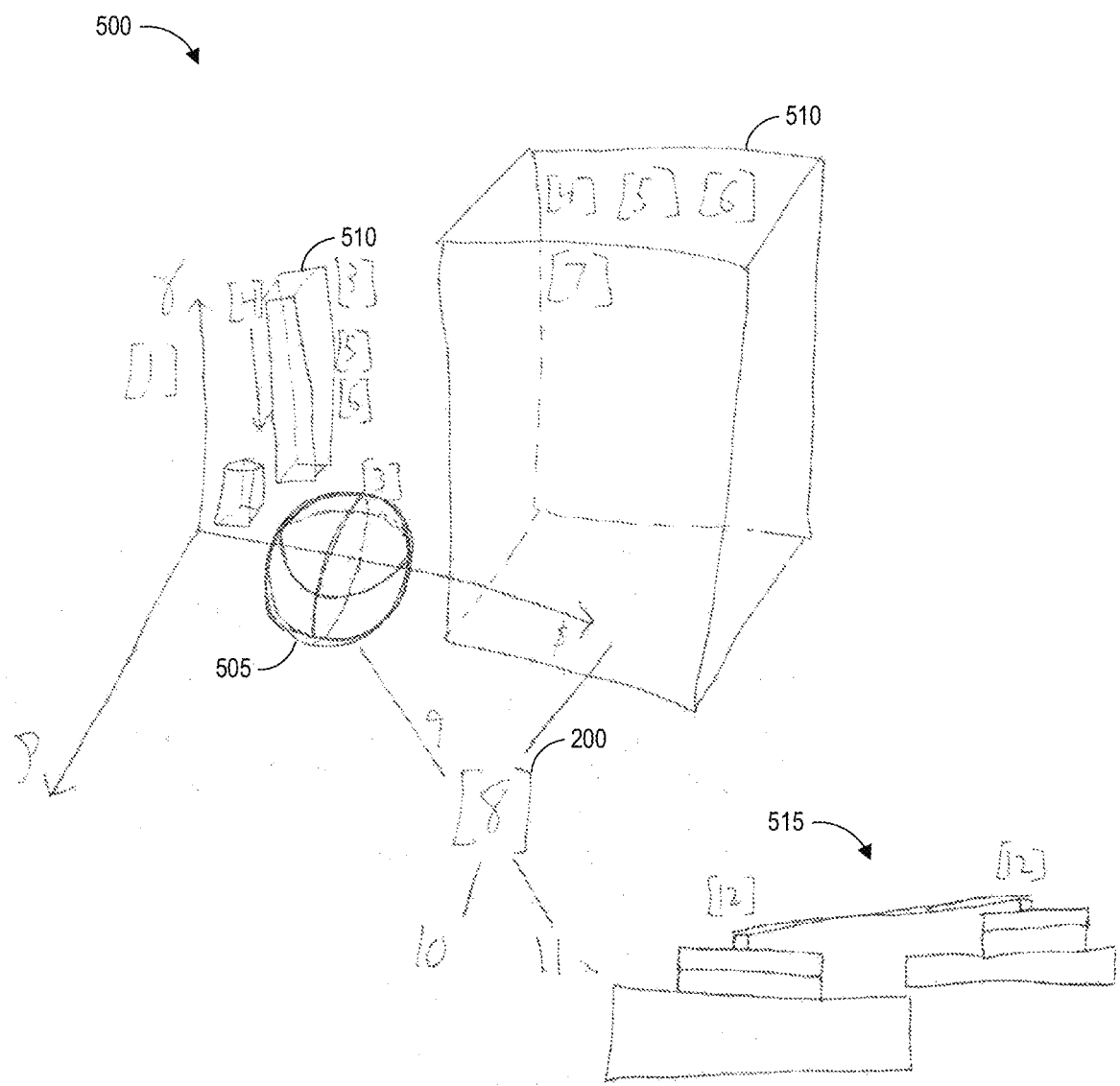
FIG. 5 is an illustration of the plotting of material properties in accordance with aspects of this disclosure.

FIG. 5 is an illustration of the plotting of material properties in accordance with aspects of this disclosure. Examples of material properties which can be plotted include: price, electrical resistance, tensile strength, etc. Each material property under consideration can be plotted on a 3D graph 500, where each axis corresponds to one of the material properties. However, when only two properties are under consideration, a 2D graph can be generated. When certain materials have variable properties, the range of possible properties can also be illustrated, rather than a scatter point plot.

The plotting of material properties as illustrated in FIG. 5 can be performed to select a material for use in molecular structure design. For example, the user can plot a plurality of material properties, and based on a visualization of the properties, select one of the materials which meets the material property requirements required by the particular application.

In the specific example of FIG. 5, the $-axis can represent the cost of the materials, the ρ-axis can represent the electrical resistance, and the γ-axis can represent tensile strength. A variable material property 505 is shown illustrated roughly by a sphere. Other material properties 510 which may affect the plotted variable properties can be overlaid on the on the graph. Examples of these properties include: grain size, microstructure, dislocations, thermodynamic data, etc. The user can select a material using a 6DoF controller 200 and use the selected material in the design of a molecular structure, as described above.

Interaction with the VR environment can be accomplished by traditional VR interactive techniques. Selection technique, indication of selected object, confirmation of selection (e.g., confirmation of the selection of: event, gesture, voice command, or no explicit command), feedback to user based on selection (which can include text, symbolic, aural, visual, force, and/or tactile feedback). The indication of an object can require a determination of whether the object is occluded, if the object is touching another object, what the user is point to, an indirect selection of an object, selection of a list of objects (e.g., a set of objects, automatically selected set of objects, iconic objects, etc.), selection based on 2D gaze of the user, 3D gaze, 3D hand selection. Movement of a selected object can also be based on one-to-one hand to object movements or can be mapped to other aspects of the user's hand movement, such as, mapping positional changes to velocity of user movement, movement at a distance from the user's hands, etc.

The placement of the user within a virtual environment can also be performed in accordance with a traditional VR environmental manipulation technique. Such techniques include: exocentric metaphors, world-in-mini-game, automatic scaling, egocentric metaphors, virtual hand metaphors, "classical" virtual hand, Go-Go technique, indirect Go-Go technique, virtual pointer metaphors, ray-casting, aperture, flashlight, image plane, hand-centered object manipulation extended ray-casting, scaled-world grab, Voodoo dolls, etc.

Applications of Molecular Simulation and Design

Molecular structures designed by the aspects described herein can be used in a number of different applications. For example, once the size of a given structure is greater than a certain threshold, the structure can be printed by a 3D printer. Although 3D printing has a limit on the resolution of the printed objects, the structure designed using the above-described systems can be printed when the structure's size is greater than the 3D printer's resolution.

Quantum Dots

The system 100 described herein can also be used to design structures using quantum dots. Quantum dots (QDs) are spherical, semiconducting nanoparticles typically between two and ten nanometers in characteristic dimension that fluoresce in response to incident ultraviolet light. The optical properties of QDs predominantly depend on one of two properties: particle size and particle composition. By varying the relative size of the former class of QDs nanoparticles, the emission wavelength of the fluorescent photons can be altered. Decreasing the size (of a given composition) of the former class of QD nanoparticles increases both the quantum confinement it experiences in all three physical dimensions and the separation between its electronic conduction and valence bands (e.g., band gap); this decrease in size manifests as a decrease in wavelength (or increase in energy) of the emitted fluorescent photon.

The latter class of QDs experiences changes in electronic band structure in response to changes in the relative amounts of constituent atoms. For example, cadmium-selenidesulfide (CdSxSe1-x) nanoparticles of a given size can exhibit a range of fluorescence emission wavelengths simply by altering the relative ratio of sulfur atoms to selenide atoms. Therefore, two general classes of QDs are those which utilize variations in particle size at a constant composition to elicit fluorescent photons of different wavelengths and those which utilize variations in composition at a constant particle size to achieve similar ends.

The described technology provides a working model for the first class of QD nanoparticles. The user of the system 100 is capable of altering the size of a QD particle to achieve the desired fluorescence emission wavelength according to the Brus equation, using the 6DoF input methods described herein. The Brus equation is provided below:

$$\Delta E(r) = E_{gap} + \frac{h^2}{Sr^2}(1/m_e^* + 1/m_h^*)$$

where $\Delta E(r)$ is the estimated energy of a fluorescent photon, h is Planck's constant, r is the radius of the QD, $E_{gap}$ the bulk band gap energy of the QD material, $m_e^*$ is the effective mass of an electron (in the exciton generated upon absorbance of incident light within a given material), and $m_h^*$ is the effective mass of a hole (in the same exciton).

The described technology also provides a working model for the second class of QD nanoparticles in which the user can directly vary the composition of relevant constituent atoms in order to achieve the desired fluorescence emission wavelength. Calculations pertaining to both classes of QDs are material-dependent, meaning that relevant equations typically rely on specific material properties. The described technology enables the user to access relevant databases for the purpose of designing QD nanoparticles with the desired properties. An exemplary list of QD materials includes Si, CdSe, CdSSe; however, this list is not exhaustive. The designed QD nanoparticles can be coated in other materials, such as zinc-sulfide. Depicting, modeling, and simulating the storage and interactions of these structures with each other, the solvent of choice, and other structures created using the described technology is also within the scope of this disclosure.

Node-Placement Molecular Model

The design of molecules and molecular structures as interactive 3D visualizations in a VR environment is another application of this disclosure. The node-placement molecular model enables the user to place carbon atoms as nodes in any point in the user's interactive VR environment. Aspects of this disclosure enable a user to place a single bond between successively placed nodes; the remainder of the four chemical bonds available at each carbon node can be attached to hydrogen atoms by default, depicting an alkane structure.

The system 100 provides functionality to the node-placement molecular model to simplify the design of organic structures. The user is able to specify double- and triple-bonds where desired along the molecule. An automated mode takes into account the exact bond lengths between all atoms in the system, and can be automatically simulated by the system 100 in response to the placement of atoms by the user. These bond lengths depend predominantly on the constituent atoms and the electronic orbitals housing bonding electrons. In this automated mode, the user can draw a line of a given length; the ratio of that length to the interatomic bond length, to the nearest integer whole number, can be used to determine the number of nodes to place. This feature removes the user's burden of positioning nodes at the proper length manually.

The range of atoms available to the user in the node-placement molecular model encompasses all atoms. This can be provided via access to elemental databases. All recognized types of chemical bonds (covalent, ionic, and metallic) can also be incorporated into the node-placement molecular model as well. Types of physical bonds (Keesom, Debye, and London forces, hydrogen-bonding, electrostatic double layer forces, solvent-solute interactions, Coulombic interactions among others) are also incorporated into this disclosure to enable the simulation and/or modeling of multiple user-designed molecules.

Mathematical Visualization

Aspects of this disclosure can also be applied to mathematical model simulation, and in particular, to a 3D graphing calculator in VR. Using the 6DoF input devices and systems described herein, a user of the system 100 can create: vector visualizations, vector cross product, graph single and multivariable functions, contours projection on surfaces, tangent planes of functions, input in Cartesian, cylindrical, spherical coordinates, parametrized curves, partial derivatives and directional derivatives, Riemann visualization in R3, visualize curl, and/or visualize flux.

Example Flowchart for Simulating a Molecular Structure

Figure 6:
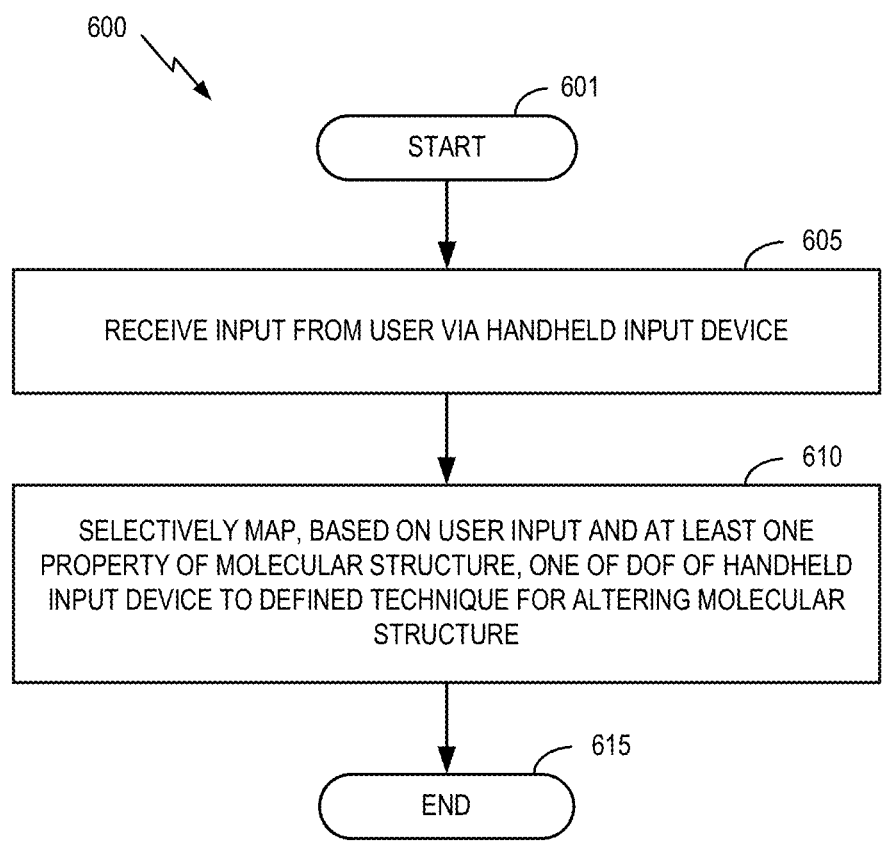
FIG. 6 is a flowchart illustrating example method operable by a handheld input device for simulating a molecular structure in accordance with aspects of this disclosure.

FIG. 6 is a flowchart illustrating example method operable by a handheld input device of the system 100, or component(s) thereof, for simulating a molecular structure in accordance with aspects of this disclosure. For example, the steps of method 600 illustrated in FIG. 6 can be performed by a processor 110 of the system 100 and/or a processor 250 of an input device 120, such as the controller 200. For convenience, the method 600 is described as performed by the processor 250 of the controller 200.

In one implementation, the system 100 comprises a processor 110 configured to simulate the molecular structure, a display, such as output device(s) 125, and at least one handheld input device. The method 600 begins at block 601. At block 605, the processor 250 receives input from a user of the system 100. The input can be indicative of movement of the handheld input device in 6 degrees-of-freedom (DoF). At block 610, the processor can selectively map, based on additional user input and at least one property of the molecular structure, one of the DoF to one of a plurality of defined techniques for altering the molecular structure. The additional user input may, for example, include the user actuating a button formed on the handheld input device. The method 600 ends at block 615.

Implementations

Certain implementations for molecular design and simulation have been presented above. The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details. Thus, the present invention is not intended to be limited to the implementations shown herein but is to be accorded the widest scope consistent with the principles and novel features disclosed herein.

What is claimed is:

1. A system for simulating a molecular structure, comprising:
   a processor;
   a head-mounted display (HMD);
   at least one handheld input device; and
   a non-transitory computer readable storage medium having stored thereon instructions which, when executed by the processor, cause the processor to:
   simulate the molecular structure,
   instruct the HMD to display the molecular structure,
   receive input from a user via the at least one handheld input device, the input being indicative of movement of the handheld input device in 6 degrees-of-freedom (DoF),
   map, based on additional user input and at least one property of the molecular structure, at least one of the DoF to one of a plurality of defined techniques for altering the molecular structure,
   alter the molecular structure based on the received input and the mapping of the one of the DoF to the one of the defined techniques, and
   determine whether the type of the molecular structure is a crystalline molecular structure,
   wherein the mapping of the at least one of the DoF comprises mapping three translational DoF of the handheld input device to three scaling values that define the scale of the molecular structure along three axes in response to determining that the type of the molecular structure is the crystalline molecular structure and
   wherein the scaling of the molecular structure along one of the three axes comprises increasing or decreasing the number of particles comprising the molecular structure in the one of the three axes.

2. The system of claim 1, wherein modifying the molecular structure using the one of the defined techniques comprises applying a transformation matrix to the molecular structure and wherein the mapping the at least one of the DoF to the one of the defined techniques comprises mapping changes in the one of the DoF to changes to one of a plurality of values of the transformation matrix.

3. The system of claim 1, wherein the mapping of the at least one of the DoF further comprises mapping at least one rotational DoF of the handheld input device to a Miller plane of the crystalline structure.

4. The system of claim 3, wherein the non-transitory computer readable storage medium further has stored thereon instructions which, when executed by the processor, cause the processor to instruct the HMD to display a resistance value of the crystalline structure in response to the user moving the handheld device in the at least one rotational DoF.

5. The system of claim 1, wherein the non-transitory computer readable storage medium further has stored thereon instructions which, when executed by the processor, cause the processor to determine whether the type of the molecular structure is a carbon nanotube, wherein the mapping of the at least one of the DoF comprises mapping only one of the translational DoF of the handheld input device to a scaling value that defines the scale of the molecular structure along the length of the carbon nanotube.

6. The system of claim 5, wherein the mapping of the at least one of the DoF comprises mapping at least one rotational DoF of the handheld input device to a value indicative of the chirality of the carbon nanotube.

7. The system of claim 6, wherein the non-transitory computer readable storage medium further has stored thereon instructions which, when executed by the processor, cause the processor to instruct the HMD to display a resistance value of the carbon nanotube in response to the user moving the handheld device in the at least one rotational DoF.

8. The system of claim 1, wherein the non-transitory computer readable storage medium further has stored thereon instructions which, when executed by the processor, cause the processor to:
instruct the HMD to display a graph of properties of a plurality of materials selectable by the user,
receive a selection of one of the materials from the user via the at least one handheld input device, and
instruct the HMD to display the molecular structure in response to the selection of the one of the materials.

9. The system of claim 1, wherein the at least one handheld device further comprises a button and wherein the non-transitory computer readable storage medium further has stored thereon instructions which, when executed by the processor, cause the processor to toggle activation of the selective mapping based on actuation of the button by the user.

10. A system for simulating a molecular structure, comprising:
a processor;
at least one handheld input device; and
a non-transitory computer readable storage medium having stored thereon instructions which, when executed by the processor, cause the processor to:
simulate the molecular structure,
receive input from a user via the at least one handheld input device, the input being indicative of movement of the input device in 6 degrees-of-freedom (DoF),
map, based on additional user input and at least one property of the molecular structure, at least one of the DoF to one of a plurality of defined techniques for altering the molecular structure,
alter the molecular structure based on the received input and the mapping of the one of the DoF to the one of the defined techniques, and determine whether the type of the molecular structure is a crystalline molecular structure,
wherein the mapping of the at least one of the DoF comprises mapping three translational DoF of the handheld input device to three scaling values that define the scale of the molecular structure along three axes in response to determining that the type of the molecular structure is the crystalline molecular structure and
wherein the scaling of the molecular structure along one of the three axes comprises increasing or decreasing the number of particles comprising the molecular structure in the one of the three axes.

11. The system of claim 10, wherein modifying the molecular structure using the one of the defined techniques comprises applying a transformation matrix to the molecular structure and wherein the mapping the at least one of the DoF to the one of the defined techniques comprises mapping changes in the one of the DoF to changes to one of a plurality of values of the transformation matrix.

12. The system of claim 10, wherein the the mapping of the at least one of the DoF further comprises mapping at least one rotational DoF of the handheld input device to a Miller plane of the crystalline structure.

13. The system of claim 12, wherein the non-transitory computer readable storage medium further has stored thereon instructions which, when executed by the processor, cause the processor to instruct a head-mounted display (HMD) to display a resistance value of the crystalline structure in response to the user moving the handheld device in the at least one rotational DoF.

14. A method of simulating a molecular structure, comprising:
generating a virtual-reality (VR) video stream including the molecular structure;
receiving input from at least one handheld device, the received input being indicative of movement of the handheld input device in 6 degrees-of-freedom (DoF);
mapping, based on additional user input and at least one property of the molecular structure, at least one of the DoF to one of a plurality of defined techniques for altering the molecular structure;
altering the molecular structure based on the received input and the mapping of the one of the DoF to the one of the defined techniques, and
determining whether the type of the molecular structure is a crystalline molecular structure,
wherein the mapping of the at least one of the DoF comprises mapping three translational DoF of the handheld input device to three scaling values that define the scale of the molecular structure along three axes in response to determining that the type of the molecular structure is the crystalline molecular structure and
wherein the scaling of the molecular structure along one of the three axes comprises increasing or decreasing the number of particles comprising the molecular structure in the one of the three axes.

15. The method of claim 14, further comprising:
applying a transformation matrix to the molecular structure, wherein the mapping the at least one of the DoF to the one of the defined techniques comprises mapping changes in the one of the DoF to changes to one of a plurality of values of the transformation matrix.

16. The method of claim 14, wherein the mapping of the at least one of the DoF further comprises mapping at least one rotational DoF of the handheld input device to a Miller plane of the crystalline structure.

17. The method of claim 16, further comprising:
displaying a resistance value of the crystalline structure in response to the user moving the handheld device in the at least one rotational DoF.

* * * * *